(12) United States Patent
Vega

(10) Patent No.: US 6,879,707 B2
(45) Date of Patent: Apr. 12, 2005

(54) PLURAL COLORANTS IN FLOW TRACER/DEBUGGER

(75) Inventor: Ramon Vega, Sabadell Barcelona (ES)

(73) Assignee: Hewlett-Packard Development Company, L.P., Houston, TX (US)

( * ) Notice: Subject to any disclaimer, the term of this patent is extended or adjusted under 35 U.S.C. 154(b) by 466 days.

(21) Appl. No.: 09/733,832

(22) Filed: Dec. 5, 2000

(65) Prior Publication Data

US 2002/0106110 A1 Aug. 8, 2002

(51) Int. Cl.[7] .................................................. G06K 9/00
(52) U.S. Cl. ..................... 382/107; 73/170.07; 382/154
(58) Field of Search .................... 382/100, 107, 382/154, 162, 163, 164, 165, 166, 167, 228; 73/1.24, 170.04, 170.07, 227, 418, 861.05, 861.07; 137/240, 340; 406/14, 30, 144; 356/246, 409

(56) References Cited

U.S. PATENT DOCUMENTS

| | | | | |
|---|---|---|---|---|
| 3,676,538 A | * | 7/1972 | Patterson | ..................... 264/75 |
| 3,851,798 A | * | 12/1974 | Miller | ......................... 222/135 |
| 5,249,238 A | * | 9/1993 | Kormerath | ................... 382/107 |
| 6,129,872 A | * | 10/2000 | Jang | ............................. 264/75 |
| 6,182,685 B1 | * | 2/2001 | Goff et al. | .................. 137/340 |
| 6,543,490 B1 | * | 4/2003 | Owens | ......................... 141/20 |

* cited by examiner

*Primary Examiner*—Bhavesh M. Mehta
*Assistant Examiner*—Abolfazl Tabatabai
(74) *Attorney, Agent, or Firm*—Peter I. Lippman

(57) ABSTRACT

An array of colorant nozzles, filled with different colors, is placed at an enclosure through which fluid flow is to be analyzed. The array injects the colors into the enclosure with the flow. Color paths through the enclosure are observed and analyzed. The array best spans the enclosure two-dimensionally and injects different colors at different portions of the channel. Controlled timing of injection, e. g. in pulses, and synchronous detection—including tracking leading/trailing ends of color pulses in the enclosure—is best. Specific spatial-temporal color patterns, and 3D observations (as by plural cameras, aimed through windows or a transparent wall, or inside the disclosure) are preferred. For very large systems a careful, exact scale model is used. Preferably a programmed processor operates the array and controls analysis of resulting observed color patterns in the fluid.

20 Claims, 3 Drawing Sheets

PLURAL COLORANTS IN FLOW TRACER/DEBUGGER

RELATED PATENT DOCUMENT

A closely related document is a coowned U.S. utility patent application—hereby incorporated by reference in its entirety, entitled "THREE- AND TWO-DIMENSIONAL IMAGES FORMED BY SUSPENDED OR TRANSITORY COLORANT IN A VOLUME", filed generally contemporaneously herewith and later assigned application Ser. No. 09/729,549, of Ramón Vega et al., and issued as U.S. Pat. No. 6,614,768.

FIELD OF THE INVENTION

This invention relates generally to machines and procedures for tracing flow lines of a moving fluid; and more particularly to determining such flow patterns with an eye to correcting any undesired characteristics such as turbulence or eddies.

BACKGROUND OF THE INVENTION

Flow monitoring is known for many different kinds of enclosures, ranging in scale from microscopic to titanic. Thus for example flow imaging is undertaken to determine obstructions in blood vessels of infants, to determine flow vs. shock characteristics in wind tunnels with installed fluid-interacting shapes (often as scale models) of aircraft wings, submarine hulls or battleships; to evaluate cavitation potential in pump stations and siphons of very large aqueducts; and to assure effective heat transfer in seawater cooling chambers of powerplants.

It is known in these applications to dye the fluid to enhance visualization of its behavior. Such a dye technique generally applies colorant continuously, or in a single color, or both.

These characteristics of the flow-monitoring technique unfortunately limit the capability to identify or to fully quantify flow-related properties that vary within the volume—such as for example eddies 12c (FIG. 1) or velocity fluctuation through the flow line, Bernoulli-effect artifacts, reentrant or spiraling paths 12b, or in some circumstances even major influences such as shock waves, or such simple phenomena as exit flows 15b, 15c that are not parallel to the major axis of the system.

Although these technologies are extremely useful and of very great societal value, nevertheless limitations in the art prevent the derived information from being as fully valuable as it could be. Thus important aspects of the technology used in the field of the invention remain amenable to useful refinement.

SUMMARY OF THE DISCLOSURE

The present invention introduces such refinement. In its preferred embodiments, the present invention has several aspects or facets that can be used independently, although they are preferably employed together to optimize their benefits.

In preferred embodiments of a first of its facets or aspects, the invention is a method for tracing or analyzing fluid flow through an enclosure. For purposes of this document (and not only this first embodiment), the word "enclosure" is to be construed very broadly—encompassing, merely by way of example, a canal, channel, tube, pipe, nozzle, vessel, fitting, adapter or chamber.

The method includes the steps of providing an array of colorant-injection elements for positioning at an enclosure; and operating the array to inject different colorants from the injection elements into the enclosure with the fluid flow. Yet another step is observing paths of the different colorants through the enclosure with the fluid flow.

The foregoing may represent a description or definition of the first aspect or facet of the invention in its broadest or most general form. Even as couched in these broad terms, however, it can be seen that this facet of the invention importantly advances the art.

In particular, this aspect of the invention enhances the incisiveness of prior methods for monitoring flow through enclosures, by introducing a capability for independent but concurrent observation of different regions in an enclosure, or different flow regimes. This is a particularly powerful technique for detecting and analyzing situations in which subflows recirculate and eddy, or join, diverge, or even cross one another. This method is compatible with various other sophisticated modes of observation and analysis such as monitoring of fluid compression and expansion, shock waves etc.

Although the first major aspect of the invention thus significantly advances the art, nevertheless to optimize enjoyment of its benefits preferably the invention is practiced in conjunction with certain additional features or characteristics. In particular, when the method is used with fluid flow that is three-dimensional, preferably the providing step include providing an array that substantially spans the enclosure two-dimensionally. Another preference is that the providing step include providing elements for injection of different colorants at different portions of the enclosure cross-section.

Yet another preference is that the operating step include controlling timing of the colorant injection, and the observing step include controlling observation synchronously with the injection. In this case it is further preferable that the timing controlling include injecting the colorant in pulses; and the observation controlling include tracking and analyzing movement, through the enclosure, of leading and trailing ends of the colorant pulses.

Still another basic preference is that the operating step include injecting the colorants in specific spatial-temporal color patterns; and the observing step include analyzing downstream movement of the specific spatial-temporal color patterns in the fluid.

Another preference is that the observing step include three-dimensional observations. It is also preferable that the observing step include observing position and direction of colorants at at least one cross-section within or exit from the enclosure.

Also preferably the method includes the step of preparing a substantially exact model of the enclosure, in which at least portions of the model wall are transparent to some propagating vibration; and that the observing step include observation through those portions, using that propagating vibration. (Allowing for a suitably broad definition of "colorant", such propagating vibration is not limited to visible light but rather may instead be IR or UV light, X-rays, radio waves, or acoustic vibration, or any other useful form of disturbance including e. g. such relatively exotic types as nuclear magnetic resonance.) Preferably the observing step includes observation through the portions by plural cameras.

Another preference is that the method further include forming at least one window in the enclosure; and that the observing step include observation through the at least one window. Still another preference is that the method also include mounting at least one camera within the enclosure; and that the observing step include making pictures with the at least one camera.

In preferred embodiments of its second major independent facet or aspect, the invention is apparatus for tracing or analyzing three-dimensional fluid flow. (Please note that, unlike the first aspect, this second one may be independent of any enclosure.)

The apparatus includes an array of colorant-injection elements for positioning in the fluid flow, Pith two dimensions of the array extended transversely of a flow direction. Also included in the apparatus is a programmed processor operating the array to inject different colorants from the injection elements into the flow in specific spatial-temporal color patterns.

The foregoing may represent a description or definition of the second aspect or facet of the invention in its broadest or most general form. Even as couched in these broad terms, however, it can be seen that this facet of the invention importantly advances the art.

In particular, use of specific patterns of colorant in space and time enables detection and quantification of much more subtle and complicated flow conditions. With care in design of the input colorant pattern and its later monitoring, in effect each different colorant condition can be made to act as a semiindependent probe parameter.

Although the second major aspect of the invention thus significantly advances the art, nevertheless to optimize enjoyment of its benefits preferably the invention is practiced in conjunction with certain additional features or characteristics. In particular, preferably the specific patterns include injection of at least some of the colorants in multiple successive pulses.

Another preference is that the apparatus also include some means for observing three-dimensional movement of the specific spatial-temporal color patterns in the fluid flow. For purposes of breadth and generality in discussion of the invention, these means will be called simply the "observing means".

In preferred embodiments of its third major independent facet or aspect, the invention is apparatus for tracing or analyzing fluid flow in a very large or very small environment. The apparatus includes an accurate scale model of the environment, including the fluid flow.

It also includes an array of colorant-injection elements for positioning in such scale-model fluid flow with at least one dimension of the array extended transversely of a flow direction. The apparatus further includes a programmed processor operating the array to inject different colorants from the injection elements into the scale-model flow, in specific spatial-temporal color patterns.

The foregoing may represent a description or definition of the third aspect or facet of the invention in its broadest or most general form. Even as couched in these broad terms, however, it can be seen that this facet of the invention importantly advances the art.

In particular, this form of the invention exploits the capabilities of the above-discussed aspects to enable exploration of flow environments that are much too small or large for effective direct observation. People skilled in this field will understand that well-known techniques of scaling must be used with care to account for different temporal behavior of objects and media at diverse scales.

Although the third major aspect of the invention thus significantly advances the art, nevertheless to optimize enjoyment of its benefits preferably the invention is practiced in conjunction with certain additional features or characteristics. In particular, when used in analyzing fluid flow that is three-dimensional this facet of the invention preferably also includes some means for observing three-dimensional movement of the specific spatial-temporal color patterns in the fluid flow; and preferably the array is positioned with two dimensions of the array extended transversely of the flow direction.

Another preference is that the environment include a blood vessel, lymphatic duct, powerplant coolant tunnel, canal for oceangoing ships, or other very large or very small chamber. (In broadest form, this third aspect of the invention does not necessarily include any chamber.)

An alternative preference is that the environment include fluid around a ship, submarine, aircraft, or other fluid craft; and that the scale model include a scale model of the ship, submarine, aircraft, or other fluid craft. Still another preference is that the specific patterns include injection of at least some of the colorants in multiple successive pulses.

All of the foregoing operational principles and advantages of the present invention will be more fully appreciated upon consideration of the following detailed description, with reference to the appended drawings, of which:

DETAILED DESCRIPTION OF THE PREFERRED EMBODIMENTS

1. Colorant Injection

A particularly advantageous strategy—though not a requirement of the present invention—for injecting colorant in a very highly controlled and extremely versatile way is to apply the techniques and teachings of thermal-inkjet technology, particularly such as developed and extensively refined by the Hewlett Packard Company. These teachings are set forth in many patents assigned to Hewlett Packard, and encompass use of an electrical heating resistor to vaporize a bubble of colorant and so to forcibly expel a quantum of the colorant, ahead of the bubble, from a nozzle.

For each color, a common tank supplies colorant to replenish an ejection nozzle thus equipped, through a network of supply channels within an ejection head. Thermal-inkjet technique developed by Hewlett Packard also encompasses specialized high-volume production methods for key components of very-small-scale ejection heads—particularly tape-automated bonding ("TAB") nozzle plates, and unitary silicon-chip construction for the heaters and supply channels within the head.

These teachings are also adaptable for larger-scale systems such as some of the large flow installations mentioned in this document. Also encompassed within these teachings and applicable here are methods for multiplexing and demultiplexing of firing signals to a multiple-nozzle head that is at a distance from a controlling processor.

Figure 1:
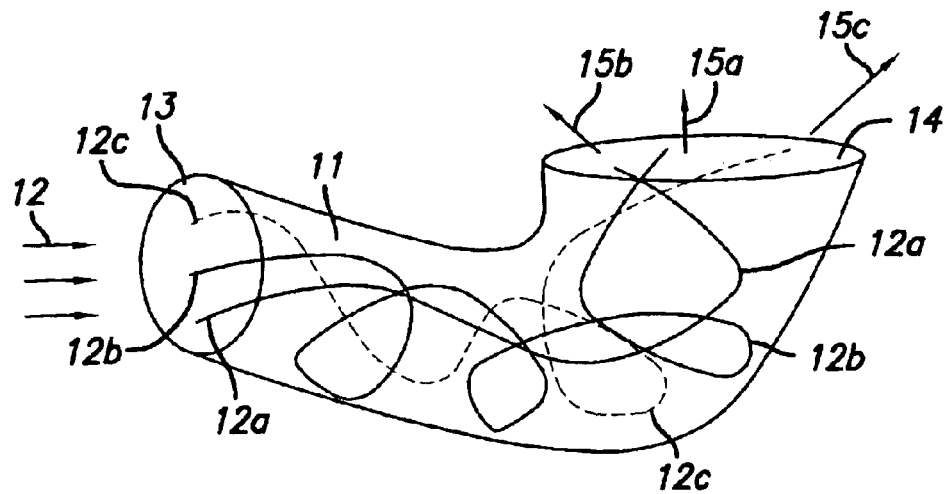
FIG. 1 is a highly schematic isometric or perspective view of fluid flows considered to be within see-through walls of a representative enclosure—a pipe, tube, canal, channel, nozzle, vessel, fitting, adapter or chamber; or a wind tunnel; or a blood vessel, lymphatic duct, powerplant coolant tunnel, canal for oceangoing ships, or other extremely large or small chamber; or the immediate environment around a ship, submarine, aircraft or other fluid craft; or any other enclosure in which fluid flow is of interest.
Figure 7:
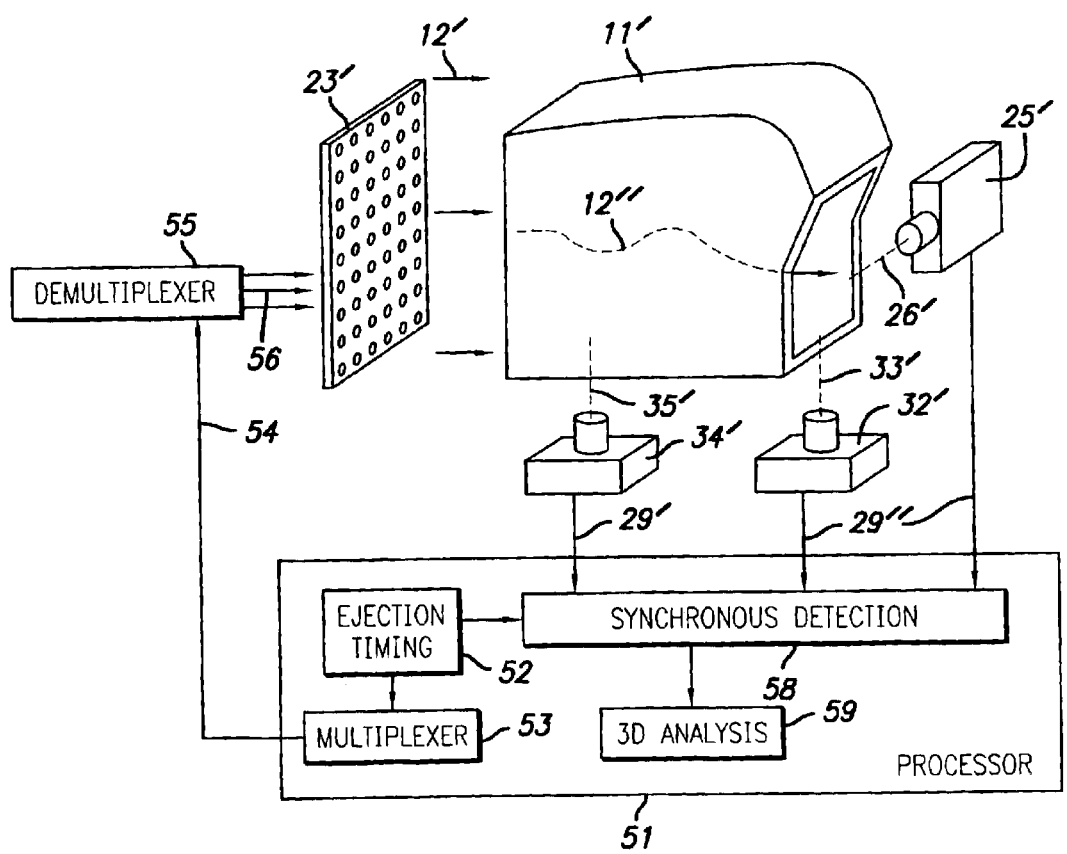
FIG. 7 is a representation, quite schematic, of preferred artificial-flow embodiments of the invention, partially alternative to the FIG. 2 embodiments.

Two main approaches to the introduction of colorant into a test enclosure are:

injecting colorant into, or in other words superposing the colorant upon, a natural or existing, operational flow 12 (FIGS. 1 and 2); and providing colorant as—or as part of—an artificially generated flow 12' (FIG. 7).

Each of these basic techniques has its own benefits and drawbacks. Although the drawings show colorant injection at an entrance of the enclosure, this is by no means a necessary condition: injection can be provided at internal points instead, or in addition.

An advantage of the operational-flow approach is that it tends to take account of any peculiarities in the incident flow, from whatever source is upstream of the test enclosure. Such peculiarities include, for example, thermal gradients, chemical characteristics and even physical properties that actually influence flow in the subject enclosure—particularly important if they influence the flow in unexpected ways.

Figure 5:
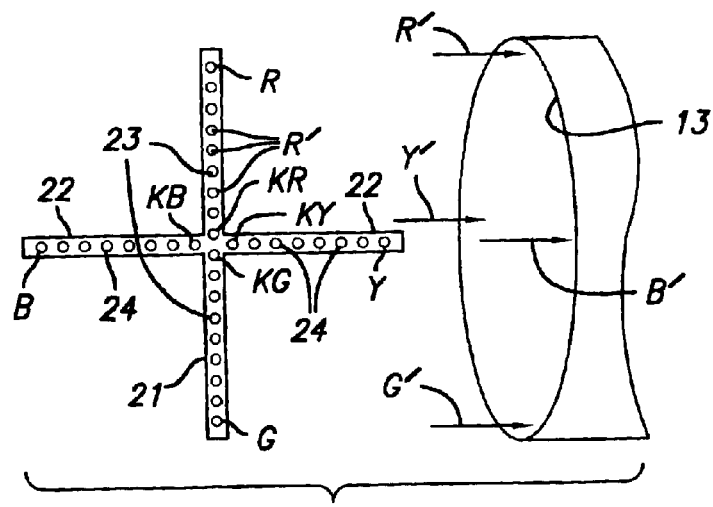
FIG. 5 is a right elevation of the FIG. 2 colorant-injection array, for creating highly specific spatial patterns of colorant—together with colorant flow from the array into the FIG. 2 enclosure entrance.

A disadvantage of this approach is that it requires installation of colorant-injecting hardware 21–24 (FIGS. 2 and 5) into the natural flow 12, particularly in such a way that the hardware does not itself perturb the flow phenomena that are to be measured. This consideration is suggested in the drawings by showing the hardware as in the form of two very thin foils 21, 22, each with streamlined cross-section.

Colorant is advantageously ejected from fine nozzles 23, 24 arrayed along the downstream edges of the two foils. To obtain two-dimensional structure in the probe colorant, the foils are crossed orthogonally—and from time to time, if desired to probe different regions of the flow or to obtain a different analytical emphasis, the centerpoint can be shifted with respect to the system axis, or the foils rotated about that axis, or both.

An advantage of the artificial-flow approach, on the other hand, is that it undertakes to assume a greater degree control of the entire process, so that the measurements assume a more scholarly precision. In addition, complicated and subtle fluctuations or variations in measurement conditions may be more straightforwardly introduced.

A corresponding disadvantage, particularly for large systems, is typically a need to provide high volumetric flows of a subject fluid that reasonably simulates the operational flow—and possibly also to recover and recycle the colorants. In this regard some of the discussions of flow meshes, inkjet technology, and other technique in the above-mentioned related patent document will be helpful and accordingly are incorporated by reference here. (To a lesser extent those discussions may also be of interest as to the operational-flow approach.)

While deployment of particular colorants can be effected in a very great variety of different ways, again two general paradigms are important to consider. One is to design the colorant injection patterns on an ad hoc basis such as to particularly bring out and emphasize known characteristics peculiar to the subject flow and, especially, known problems.

Figure 6:
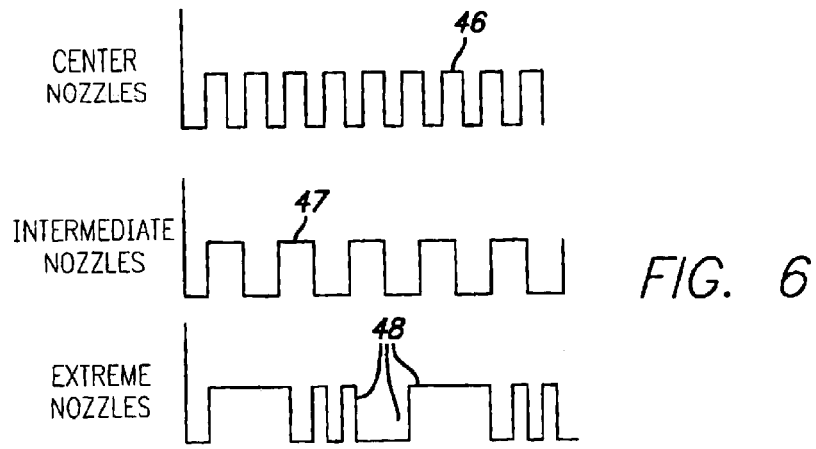
FIG. 6 is a timing diagram illustrating highly specific temporal patterns for operation of the FIG. 5 array.

Thus for instance several contrasting colorants may be discharged in very close adjacency, within a small region that is suspected to be at the root of performance difficulties—so that any possible subflows, splits and recombinations can be discovered and explored at fine resolution. Another, like option is to further refine the capability for microresolution by use of variant time modulations e. g. 46–48 (FIG. 6) in different nearby subregions within such small regions.

A contrary paradigm for colorant deployment is to establish a regular, systematic gradation of colors that can be used for most flow-analysis problems in general. This strategy facilitates development of standardized signal-analysis algorithms that enable quick and easy orientation to any entirely new fluid-flow study that arises.

Thus for example, colorants may be arrayed along one linear array 23 from a fully saturated red R (FIG. 5), at one end of that array, through red colors R' of intermediate saturation at intermediate positions along that same limb of the array, to a near-gray (i. e. red of very low saturation) kR just short of the center of the entire nozzle structure. Then from a near-gray green kG of very low saturation just beyond the center, the nozzles may eject colorant or progressively greater green saturation, proceeding in this manner to the tip of that opposite limb.

Similarly the orthogonal array 22 may be charged with colorant graded from intense blue B at one end to intense yellow Y at the other, passing through low-saturation blue kB and yellow kY near the center. In any event when the colorant-ejecting nozzles R, G, B, Y are located in some systematic fashion in an ejection array 23, 24, then the relative positions R', G', B', Y' (FIG. 5) of colorant streams entering the enclosure 13 are likewise located; and this information can be used in analysis later.

Figure 4:
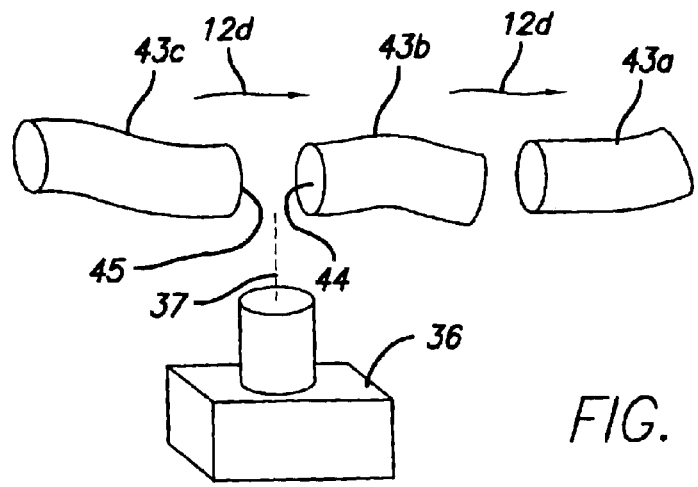
FIG. 4 is a somewhat conceptual elevation, showing observation of beginning and ending portions of colorant pulses traveling within a fluid flow.

Moreover, the colorant ejection may be continuous, or may be pulsed 43a–c (FIG. 4); and—if pulsed—the particular manner of pulsation may be used to introduce another probe dimension. For example, various modulation frequencies 46, 47 (FIG. 6) or modulation codes 48 can be used to signal origination from particular segments of the arrays 22, 23 as illustrated. If preferred, such modulation can be limited to e. g. medium- or low-saturation color regions near the middle of the crossed-array structure 22, 23.

One particularly effective use of these strategies is to operate them all, in tandem. For instance a systematic, regular color and modulation gradation—perhaps in conjunction with the previously mentioned artificial-flow technique—is in general most appropriate for a preliminary canvass of a newly begun study.

This is especially so if relatively little information about the flow is available at the outset. Then, based upon the results of that preliminary evaluation, a more finely tuned ad hoc colorant-injection pattern can be designed, possibly best in combination with the previously mentioned operational-flow technique, for a more incisive concluding study phase.

2. Colorant Monitoring and Analysis

Useful observations may be made by eye 27 (FIG. 2), with mental analysis ensuing, or by any of a great variety of camera systems 25—with signals 29 either simply recorded or displayed for later visual evaluation, or directed to computing systems 58, 59 (FIG. 7). For purposes of most passages in this discussion, those two forms of observation (i. e. direct optical and camera systems) are equivalent; exceptions will be apparent.

Observations are advantageously made at the outlet 14 of the subject enclosure, as significant information is available through even this simple form of inquiry. In addition, however, when feasible observations should be made through a window 31 formed at a suitable point in the enclosure wall—or through the wall in general if it is transparent. The concept "transparent", as suggested by the earlier discussion of this term and also the word "colorant", is meant to be flexible.

Thus the wall is said to be transparent if a vibration used for observation can pass through the wall. Different colorant substances are said to be in use if e. g. different frequencies of that vibration can be differentially absorbed or reflected by different substances used as flow tags.

In addition, for a relatively large enclosure, observations may be made by a camera (not shown) placed within the enclosure. In all cases, observations are enhanced if made in sets along complementary lines of sight, such as for example view lines 26, 28 that are orthogonal.

Many commercial and other software systems 59 are available to aid in sorting out and analyzing images made by cameras from view lines that are mutually crossing—and particularly orthogonal. Use or adaptation of these systems to take colorant implications into account will be straightforward for people skilled in the use of such software.

Figure 3:
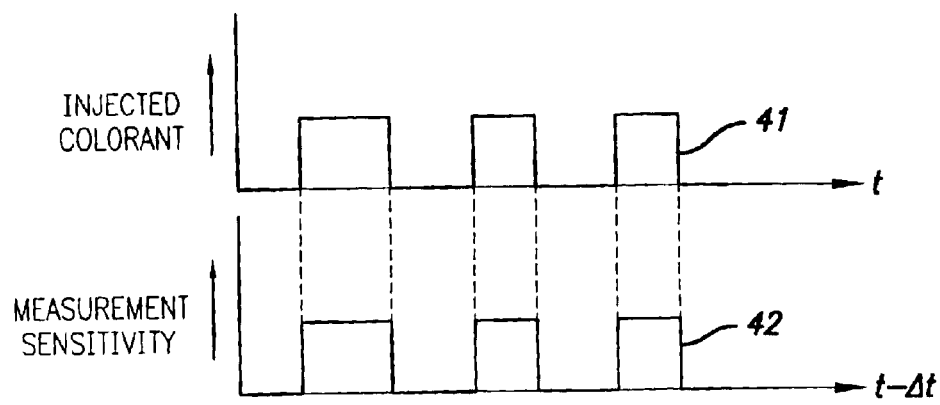
FIG. 3 is a very general timing diagram illustrating synchronization of colorant injection with colorant injection, pursuant to the invention.

In addition the invention is particularly amenable to image analysis using well-known techniques of synchronous detection 58. These techniques are roughly symbolized by a showing of coincident colorant pulses 41 (FIG. 3) and measurement-sensitivity pulses 42; however, a great body of work is available in this rather complex area.

For purposes of application to this document, it should be noted that the time axes require adjustment as for instance by subtraction of some time differential At (FIG. 3) from the measurement instant—to allow for the travel time from injection point to the particular observation point. Since in general this time interval is unknown, either it may be preliminarily measured or the system may be taught to iteratively hunt for it.

In order to apply synchronous-detection strategies, either an ejection-timing circuit 52 (FIG. 7) itself must provide signals to the detector 58, or ejection behavior should be monitored in the fluid 12, 12' very close to the ejection array 22, 23, 23' and timing signals derived from that monitoring for use in the detector 58.

Related to synchronous detection—and other temporal aspects of analysis using the present invention—is the desirability of obtaining still further flow information by examining both trailing ends 44 (FIG. 4) and leading ends 45 of at least some colorant pulses 43a–43c in a series of such pulses. By tracking variation of the gaps between trailing and leading ends it is also possible to refine assessment of local velocity.

Figure 2:
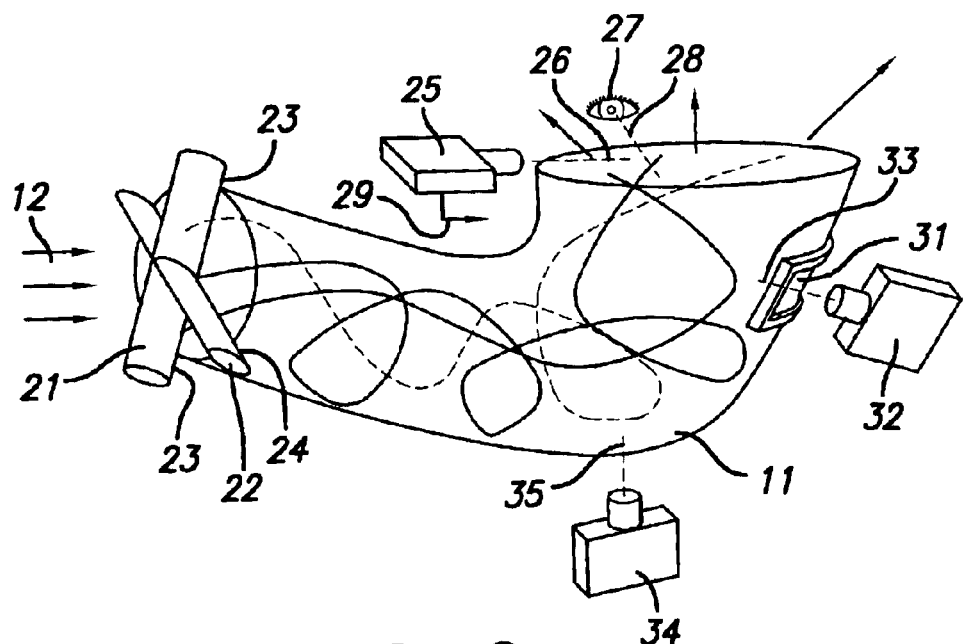
FIG. 2 is a like view of such an enclosure—or, in case it is any of the very large or small chambers mentioned, a scale model of such an enclosure—with instrumentation, particularly including a colorant-injection array at an entrance of the enclosure or model, according to preferred natural-flow embodiments of the invention.

Although generation 52 of ejection-timing signals, detection 58 and analysis 59 are explicitly shown only for the artificial-flow approach diagramed in FIG. 7, all such provisions are to be understood as also applicable in the natural-flow approach of FIG. 2. The processor 51 may itself be a digital or analog electrical type, or optical type; merely by way of example it may take the form of a general-purpose processor such as that in a general-purpose computer, with specific programming for the volume printer device in an application program stored e. g. in the computer hard drive.

Alternatively the processor may take the form of a dedicated general-purpose processor that is part of the volume printer device, and that reads programming from a read-only memory (ROM) also in that device. The processor instead may take the form of a raster image processor (RIP); or may take the form of an application-specific integrated circuit (ASIC)—or may be combinations of any two or more of these possibilities, all as well known in the inkjet and laserjet printing arts.

By exploiting the availability of different colors (and time modulation if desired), systems according to the invention achieve very high flexibility and specificity in the identification, tracing and debugging of flow lines. Several different flow lines can be tracked at the same time, and speed analyses performed easily.

Because an inked volume can be very fine in cross-section, analysis is potentially very well focused. Yet multiple characteristics of a flow regime—both independently of one another and in regard to their interactions—can be investigated and determined simultaneously.

The above disclosure is intended as merely exemplary, and not to limit the scope of the invention—which is to be determined by reference to the appended claims.

What is claimed is:

1. A method for tracing or analyzing fluid flow through an enclosure; said method comprising the steps of:

providing an array of colorant-injection elements for positioning at such enclosure;

operating the array to inject different colorants from the injection elements into the enclosure with the fluid flow; and observing paths of the different colorants through the enclosure with the fluid flow.

2. The method of claim 1, particularly for use with fluid flow that is three-dimensional; and wherein:

the providing step comprises providing an array that substantially spans the enclosure two-dimensionally.

3. The method of claim 1, wherein:

the providing step comprises providing elements for injection of different colorants at different portions of the enclosure cross-section.

4. The method of claim 1, wherein:

the operating step comprises controlling timing of the colorant injection; and the observing step comprises controlling observation synchronously with the injection.

5. The method of claim 4, wherein:

the timing controlling comprises injecting the colorant in pulses; and the observation controlling comprises tracking and analyzing movement, through the enclosure, of leading and trailing ends of the colorant pulses.

6. The method of claim 1, wherein:

the operating step comprises injecting the colorants in specific spatial-temporal color patterns; and the observing step comprises analyzing downstream movement of the specific spatial-temporal color patterns in the fluid.

7. The method of claim 1, wherein:

the observing step comprises three-dimensional observations.

8. The method of claim 1, wherein:

the observing step comprises observing position and direction of colorants at at least one cross-section within or exit from the enclosure.

9. The method of claim 1:

further comprising the step of preparing a substantially exact model of the enclosure, at least portions of the model wall being transparent to some propagating vibration; and wherein the observing step comprises observation through said portions, using said propagating vibration.

10. The method of claim 9, wherein:

the observing step comprises observation through the portions by plural cameras.

11. The method of claim 1:

further comprising the step of forming at least one window in the enclosure; and wherein the observing step comprises observation through the at least one window.

12. The method of claim 1:

further comprising the step of mounting at least one camera within the enclosure; and the observing step comprises making pictures with the at least one camera.

13. Apparatus for tracing or analyzing three-dimensional fluid flow; said apparatus comprising:

an array of colorant-injection elements for positioning in such fluid flow with two dimensions of the array extended transversely of a flow direction; and a programmed processor operating the array to inject different colorants from the injection elements into such fluid flow in specific spatial-temporal color patterns.

14. The apparatus of claim 13, wherein:

the specific patterns include injection of at least some of the colorants in multiple successive pulses.

15. The apparatus of claim 13, further comprising:

means for observing three-dimensional movement of the specific spatial-temporal color patterns in the fluid flow.

16. Apparatus for tracing or analyzing fluid flow in a very large or very small environment; said apparatus comprising:

an accurate scale model of the environment, including such fluid flow;

an array of colorant-injection elements for positioning in such scale-model fluid flow with at least one dimension of the array extended transversely of a flow direction; and a programmed processor operating the array to inject different colorants from the injection elements, into such scale-model fluid flow in specific spatial-temporal color patterns.

17. The apparatus of claim 16, particularly for use in analyzing fluid flow that is three-dimensional; and further comprising:

means for observing three-dimensional movement of the specific spatial-temporal color patterns in the fluid flow; and wherein the array is positioned with two dimensions of the array extended transversely of the flow direction.

18. The apparatus of claim 16, wherein:

the environment comprises a blood vessel, lymphatic duct, powerplant coolant tunnel, canal for oceangoing ships, or other very large or very small chamber.

19. The apparatus of claim 16, wherein:

the environment comprises fluid around a ship, submarine, aircraft, or other fluid craft; and the scale model includes a scale model of the ship, submarine, aircraft, or other fluid craft.

20. The apparatus of claim 16, wherein:

the specific patterns include injection of at least some of the colorants in multiple successive pulses.

* * * * *